United States Patent
Kubota et al.

(10) Patent No.: US 11,771,640 B2
(45) Date of Patent: Oct. 3, 2023

(54) WATER-IN-OIL EMULSION COSMETIC

(71) Applicant: Shiseido Company, Ltd., Tokyo (JP)

(72) Inventors: Shun Kubota, Kanagawa (JP); Shoko Ogawa, Kanagawa (JP); Ryushi Fukuhara, Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 17/042,606

(22) PCT Filed: Mar. 29, 2019

(86) PCT No.: PCT/JP2019/014086
§ 371 (c)(1),
(2) Date: Sep. 28, 2020

(87) PCT Pub. No.: WO2019/189796
PCT Pub. Date: Oct. 3, 2019

(65) Prior Publication Data
US 2021/0093544 A1 Apr. 1, 2021

(30) Foreign Application Priority Data
Mar. 29, 2018 (JP) ................... 2018-063662

(51) Int. Cl.
*A61K 8/02* (2006.01)
*A61K 8/06* (2006.01)
(Continued)

(52) U.S. Cl.
CPC ............ *A61K 8/8147* (2013.01); *A61K 8/025* (2013.01); *A61K 8/064* (2013.01); *A61K 8/19* (2013.01);
(Continued)

(58) Field of Classification Search
CPC ...... A61K 8/8147; A61K 8/025; A61K 8/064; A61K 8/19; A61K 8/23; A61K 8/25;
(Continued)

(56) References Cited

U.S. PATENT DOCUMENTS

| 2002/0022007 A1 | 2/2002 | Gers-Barlag et al. |
| 2003/0068285 A1* | 4/2003 | Sandewicz ............ A61Q 17/04 424/59 |

(Continued)

FOREIGN PATENT DOCUMENTS

| JP | 2000-095636 A | 4/2000 |
| JP | 2003-055143 A | 2/2003 |

(Continued)

OTHER PUBLICATIONS

Machine Translation of JP2011256154A by J-Plat Pat; https://www.j-platpat.inpit.go.jp/ (Year: 2011).*

(Continued)

*Primary Examiner* — Isaac Shomer
*Assistant Examiner* — Amanda Michelle Petritsch
(74) *Attorney, Agent, or Firm* — Foley & Lardner LLP

(57) ABSTRACT

The purpose of the present invention is to provide a water-in-oil type emulsion cosmetic that has a replenishing and smooth feel-of-use, that, once applied, forms a uniform coating, and that can minimize the appearance of skin roughness such as pores while covering discoloration such as spots and freckles, but that does not give an impression of a thick coating. The present invention provides a water-in-oil type emulsion cosmetic characterized by containing (A) 0.1-20 mass % of metallic soap-treated powder, and (B) a water-absorptive polymer having 0.01-2 mass % of a carboxyl group. The (B) water-absorptive polymer having a carboxyl group of this cosmetic preferably can absorb 10-1,000 times its own weight.

10 Claims, 2 Drawing Sheets

(51) Int. Cl.
*A61K 8/19* (2006.01)
*A61K 8/23* (2006.01)
*A61K 8/26* (2006.01)
*A61K 8/27* (2006.01)
*A61K 8/31* (2006.01)
*A61K 8/34* (2006.01)
*A61K 8/36* (2006.01)
*A61K 8/37* (2006.01)
*A61K 8/41* (2006.01)
*A61K 8/73* (2006.01)
*A61K 8/81* (2006.01)
*A61K 8/891* (2006.01)
*A61K 8/892* (2006.01)
*A61Q 1/02* (2006.01)
*A61Q 1/12* (2006.01)
*A61Q 17/04* (2006.01)
*A61K 8/25* (2006.01)
*A61K 8/29* (2006.01)
*A61Q 19/00* (2006.01)

(52) U.S. Cl.
CPC ............... *A61K 8/23* (2013.01); *A61K 8/25* (2013.01); *A61K 8/26* (2013.01); *A61K 8/27* (2013.01); *A61K 8/29* (2013.01); *A61K 8/31* (2013.01); *A61K 8/34* (2013.01); *A61K 8/345* (2013.01); *A61K 8/347* (2013.01); *A61K 8/361* (2013.01); *A61K 8/375* (2013.01); *A61K 8/416* (2013.01); *A61K 8/732* (2013.01); *A61K 8/735* (2013.01); *A61K 8/891* (2013.01); *A61K 8/892* (2013.01); *A61Q 1/02* (2013.01); *A61Q 1/12* (2013.01); *A61Q 17/04* (2013.01); *A61Q 19/007* (2013.01); *A61K 2800/546* (2013.01)

(58) Field of Classification Search
CPC .............. A61K 8/26; A61K 8/27; A61K 8/29; A61K 8/31; A61K 8/34; A61K 8/345; A61K 8/347; A61K 8/361; A61K 8/375; A61K 8/416; A61K 8/732; A61K 8/735; A61K 8/891; A61K 8/892; A61K 8/8125; A61K 2800/546; A61K 2800/612; A61K 2800/651; A61Q 1/02; A61Q 1/12; A61Q 17/04; A61Q 19/00; A61Q 19/007
See application file for complete search history.

(56) References Cited

U.S. PATENT DOCUMENTS

| | | | |
|---|---|---|---|
| 2011/0182846 A1* | 7/2011 | Ikeda | A61Q 1/02 556/439 |
| 2016/0316806 A1 | 11/2016 | Gehin-Delval et al. | |
| 2017/0007527 A1 | 1/2017 | Ibrahim et al. | |

FOREIGN PATENT DOCUMENTS

| | | | |
|---|---|---|---|
| JP | 2006-342140 A | 12/2006 | |
| JP | 2011-256154 A | 12/2011 | |
| JP | 2016-027009 A | 2/2016 | |
| JP | 2017-060738 A | 3/2017 | |
| JP | 2017-508441 A | 3/2017 | |
| JP | 2019-038781 A | 3/2019 | |
| KR | 101784028 B1 * | 10/2017 | .............. A61K 8/73 |
| WO | WO-2019-189719 A1 | 10/2019 | |

OTHER PUBLICATIONS

Machine Translation of KR101784028 by PE2E (Year: 2017).*
Machine Translation of JP2011256154A by J-Plat Pat; https:/Awww_j-platpat.inpit.go.jo/ (Year: 2011).*
Machine Translation of KR1020170005748A by K-PION; http://kposd.kipo.go.kr:8088/up/kpion/ (Year: 2017).*
International Search Report dated Jun. 18, 2019, in PCT/JP2019/014086.
International Preliminary Report on Patentability dated Sep. 29, 2020 in PCT/JP2019/013919.

* cited by examiner

WATER-IN-OIL EMULSION COSMETIC

TECHNICAL FIELD

The present invention relates to a water-in-oil emulsion cosmetic. More specifically, the present invention relates to a water-in-oil emulsion cosmetic that has excellent skin correction effects, that does not have a cakey appearance, and that has a moist and smooth feeling in use.

BACKGROUND ART

In makeup cosmetics such as foundations, white pigments such as titanium oxide and colored pigments such as iron oxide are used for having the effects of correcting skin discoloration such as spots and freckles, and correcting skin roughness such as pores. However, although skin correction effects can be obtained by the covering power of titanium oxide or the like, the finish sometimes lacked gloss and could result in an unnaturally white finish.

Patent Document 1 proposes a makeup cosmetic that, by improving the powder ingredients that are blended, provides a natural finish having a sense of transparency close to that of bare skin while covering up blemishes in the skin. In other words, instead of or in addition to a conventional pigment powder, a composite pigment, in which the surfaces of flake-shaped alumina particles having specific shapes are coated with iron oxide, is used. However, it is indicated that, with silicone-treated titanium oxide, a sense of transparency cannot be obtained, and in order to obtain sufficient covering effects, naturalness of finish and a sense of transparency with a composite pigment, the blended amount should preferably be 10% to 35% by mass (paragraphs [0027]-[0032]).

In recent years, the demand for natural makeup having a natural finish without a cakey appearance has increased further. However, it is necessary to apply multiple layers of cosmetics such as foundations in order to sufficiently cover skin discoloration and roughness, resulting in a cakey appearance. Furthermore, conventional foundations of the oil-gel type had the problem of being difficult to spread and sticking.

On the other hand, Patent Document 2 describes that a cosmetic containing a sodium polyacrylate starch or the like having high water absorption capacity is in the form of a mousse, has a fluffy and uniquely light feeling in use, provides an excellent cooling sensation, and has excellent dispersion properties for a powder that has undergone a specific surface treatment. However, it is neither disclosed nor suggested that said cosmetic has roughness correction effects or the like.

RELATED ART

Patent Documents

Patent Document 1: JP 2001-278743 A
Patent Document 2: JP 2011-256154 A

SUMMARY OF THE INVENTION

Problem to be Solved by the Invention

In view of the above-described background art, the present invention addresses the problem of providing a water-in-oil emulsion cosmetic that has a moist and smooth feeling in use, that forms a uniform coating film after being applied, that can make skin roughness such as pores inconspicuous while covering discolorations such as spots and freckles, and that does not result in a cakey appearance.

Means for Solving the Problem

As a result of diligent research towards solving the above-mentioned problem, the present inventors discovered that a gel formed by a water-absorbing polymer having carboxyl groups, represented by sodium acrylates crosspolymer-2, sodium polyacrylate starch, and the like, which has appropriately absorbed water, forms aggregates with powders that have undergone a metal soap treatment, and these aggregates provide good and sufficient roughness correction effects, thereby completing the present invention.

In other words, the present invention provides a water-in-oil emulsion cosmetic containing: (A) 0.1% to 20% by mass of a metal soap-treated powder; and (B) 0.01% to 2% by mass of a water-absorbing polymer having carboxyl groups.

Effects of the Invention

The water-in-oil emulsion cosmetic of the present invention contains an appropriate amount of a water-absorbing polymer. Said water-absorbing polymer appropriately absorbs water and forms a gel-type aggregate. Thus, it is mousse-like and fluffy to the touch and can be lightly applied to the skin, while also forming a uniform coating film. As a result thereof, it has a moist and smooth feeling in use while not needing to be applied in multiple layers, and enables general users who do not have any special makeup skills to obtain natural makeup without a cakey appearance.

MODES FOR CARRYING OUT THE INVENTION

Figure 1:
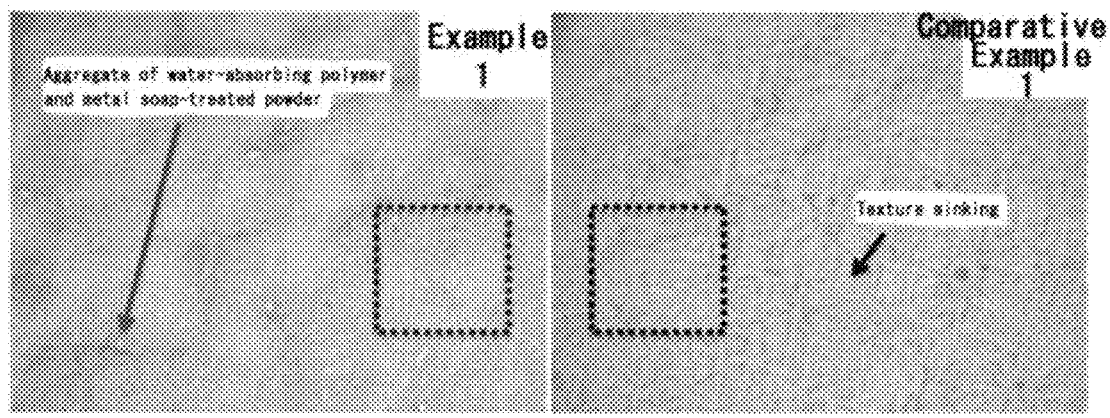
FIG. 1 is a drawing showing an image obtained by using a Skin Visiom® (an apparatus for measuring skin conditions) to observe the state of skin to which the cosmetics of Example 1 and Comparative Example 2 have been applied.

The water-in-oil emulsion cosmetic (hereinafter also referred to simply as "cosmetic") of the present invention contains, as essential ingredients, (A) a metal soap-treated powder and (B) a water-absorbing polymer having carboxyl groups.

The (A) metal soap-treated powder in the present invention is a powder obtained by using a metal soap to treat the surface of a powder that serves as a substrate (core).

The metal soap in the present invention is defined as a salt of a carboxyl group-containing compound, such as a fatty acid, with a metal having a valence of two or higher. In this case, the carboxyl group-containing compound constituting the metal soap preferably includes, for example, fatty acids having linear or branched alkyl groups, carboxyl-modified silicones, or the like, among which higher fatty acids, i.e., linear or branched carboxylic acids having 8 to 24 carbon atoms, preferably 12 to 18 carbon atoms, are preferable.

Specific examples of preferable higher fatty acids include stearic acid, isostearic acid, myristic acid, lauric acid, and the like.

The metal having a valence of two or higher constituting the metal soap is not limited, but preferable examples include trivalent metals such as aluminum and alkaline earth metals such as calcium, magnesium, and zinc.

In other words, examples of metal soaps that are preferably used as surface treatment agents include magnesium myristate, zinc myristate, magnesium stearate, zinc stearate, aluminum stearate, aluminum distearate, aluminum oleate, aluminum palmitate, aluminum laurate, aluminum myristate, aluminum dimyristate, silicone metal soaps (divalent or trivalent metal salts of organosiloxane derivatives having terminal carboxyl groups), and the like.

The method for coating the surface of the substrate powder with the metal soap is not particularly limited, and for example, the coating may be prepared by dissolving the metal soap in a volatile solvent such as isoparaffin or isopropyl alcohol, mixing the substrate powder therein, then evaporating the volatile solvent. Alternatively, the coating may be formed simply by mixing the substrate powder with the metal soap. The amount of the metal soap coating the substrate powder surface is not particularly limited, but is preferably approximately 0.5 to 10 parts by weight relative to 100 parts by weight of the substrate powder.

The substrate powder that is surface-treated with the metal soap is not particularly limited as long as it is a powder that is conventionally blended in the field of cosmetics and the like. Specific examples include one or more powders selected from among powders including white pigments, colored pigments, and extender pigments, such as titanium oxide, zinc oxide, barium sulfate, iron oxide, talc, mica, sericite, kaolin, titanated mica, Prussian blue, chromium oxide, chromium hydroxide, silica, and cerium oxide. Additionally, the shape of the powder is also not particularly limited, and may include spherical shapes, ellipsoidal shapes, crushed shapes, and the like. The powder may also be in the state of primary particles, or may form agglomerated secondary clusters.

The average particle size of the metal soap-treated powder in the present invention is also not limited, and the powder may be a pigment-grade or a fine-particle powder. For example, an extender pigment or the like such as talc, mica, or barium sulfate having an average particles size of approximately 1 μm to approximately 50 μm, or titanium oxide having an average particle size of approximately 200 nm to approximately 1 μm is preferably used. Among these, in the present invention, a powder having an average particle size of 200 nm or greater is preferably used.

In the cosmetic of the present invention, the blended amount of the (A) metal soap-treated powder is 0.1% to 20% by mass, preferably 0.5% to 15% by mass, and more preferably approximately 1% to 10% by mass. If the blended amount is less than 0.1% by mass, then sufficient screening effects for spots, freckles, and the like cannot be obtained, and if the blended amount exceeds 20% by mass, then there tends to be patchiness, resulting in an unnatural finish.

The (B) water-absorbing polymer having carboxyl groups in the cosmetic of the present invention is a homopolymer or a copolymer with monomers having carboxy groups, or a derivative thereof, and is preferably a water-absorbing polymer having a water absorption capacity of preferably at least 10 times, more preferably 10 times to 1000 times, and even more preferably 10 times to 500 times the weight thereof. If the water absorption capacity is less than 10 times the weight thereof, then the desired properties cannot be obtained, and if it exceeds 1000 times, then there is a tendency for patchiness to occur as the absorption capacity increases.

The structure of the (B) water-absorbing polymer having carboxyl groups is not particularly limited, and may be a structure having the carboxyl groups on the polymer main chain, or may be a structure having the carboxyl groups on a side chain. Preferably, a homopolymer or a copolymer (graft, block, random) produced by the polymerization of raw material monomers including acrylic acid monomers is used. Specific examples include polyacrylic acid salts including crosslinked or non-crosslinked sodium polyacrylate (for example, crosslinked sodium carbomer), sodium polyacrylate starch, and the like.

Though not particularly limited, as the water-absorbing polymer in the present invention, one that is prepared in the form of white particles and is available as a commercial product may be used. Examples of such commercial products include AQUPEC® MG N40R: Sodium Carbomer (manufactured by Sumitomo Seika Chemicals Co., Ltd.), Makimousse 12 (average particle size approximately 12 μm) (manufactured by Daito Kasei Kogyo Co., Ltd.), and Makimousse 25 (average particle size approximately 25 μm) (manufactured by Daito Kasei Kogyo Co., Ltd.), among which it is desirable to select a polymer having high water absorption properties (at least 10 times the weight thereof).

The blended amount of the (B) water-absorbing polymer having carboxyl groups in the cosmetic of the present invention is 0.01% to 2% by mass, preferably 0.05% to 1% by mass, and more preferably 0.1% to 0.5% by mass. If the blended amount is less than 0.01% by mass, then a moist and smooth feeling in use cannot be obtained, and the skin correction effects are insufficient. If the blended amount exceeds 2% by mass, then there is a tendency for "patchiness" to occur.

Though not limiting the present invention, in the cosmetic of the present invention, it is believed that the carboxyl groups in the water-absorbing polymer, of which an appropriate amount has been blended, interact with the metal present on the surface of the metal soap-treated powder to form an aggregate, and the metal soap-treated powder is enclosed inside the aggregate (gel-shaped structure), as a result of which the cosmetic of the present invention provides sufficient skin correction effects, while being insusceptible to the effect wherein the powder sinks into pores and fine wrinkles in the skin (such as sulci cutis), causing skin roughness to become more conspicuous (also known as pore sinking and texture sinking).

The cosmetic of the present invention may, in addition to the aforementioned essential ingredients (A) and (B), contain (C) a spherical powder and/or (D) a silicone elastomer.

By appropriately blending a (C) spherical powder, the feeling in use and the skin correction effects of the cosmetic can be further improved. As the spherical powder used in the present invention, it is possible to use one selected from spheroidal powders, including those that are true spheres or oblate, generally used in cosmetics.

Preferable spherical powders include, for example, spherical silicone powders, spherical silica powders, and spherical organic resin powders such as those formed from nylon, urethane, polymethyl methacrylate, polyethylene, propylene, or the like. In the present invention, it is particularly preferable to use spherical particles that have high oil absorption amounts, among which nylon spherical powders are preferable.

As the spherical powder, it is possible to use a type that is commercially available. Examples of commercially available spherical silicone powders include KSP-300 (manufactured by Shin-Etsu Chemical Co, Ltd.); Trefil E-506S, Trefil E-508, 9701 Cosmetic Powder, EP-9215 Cosmetic Powder, EP-9261 TI Cosmetic Powder, EP-9293 AL Cosmetic Powder (all of the above manufactured by Dow Corning Toray Co., Ltd.), which are (dimethicone/vinyl dimethicone) crosspolymer spherical powders; TOSPEARL™ 120A, TOSPEARL™ 145A and TOSPEARL™ 2000B (all of the above manufactured by Momentive Performance Materials Inc.), which are polymethyl silsesquioxane spherical powders; and the like.

Examples of commercially available spherical silica powders include silica microbeads P-1500 (manufactured by JGC C&C), Sunsphere® L-51 (silica particles manufactured by AGC Inc.), and the like.

Examples of commercially available spherical organic resin powders include spherical PMMA powder particles (Ganzpearl® GMX-0810, methyl methacrylate crosspolymer particles manufactured by AICA Kogyo Co., Ltd.; Microsphere M-100 and M-330, manufactured by Matsumoto Yushi Seiyaku Co., Ltd.), spherical urethane particles (Plastic Powder D-400, manufactured by Toshiki Pigment Co., Ltd.), and the like.

The blended amount of the (C) spherical powder in the cosmetic of the present invention is normally 0.1% to 30% by mass, preferably 2% to 10% by mass, and more preferably 3% to 8% by mass. If the blended amount is less than 0.1% by mass, then the effects of blending the spherical powder cannot be obtained, and if more than 30% by mass is blended, then the moistness can conversely be lost.

When the (D) silicone elastomer is blended into the cosmetic of the present invention, the suppression of the powderiness and the improvement in the moistness become even more prominent.

As the (D) silicone elastomer in the present invention, a crosslinked or non-crosslinked silicone resin powder (elastomer) may be used. Among these, a polyether-modified silicone elastomer having an emulsifying function is preferable.

Examples of crosslinked, non-emulsifying silicone elastomers include one or more crosslinked silicone resin powders such as (dimethicone/phenylvinyl dimethicone) crosspolymer, (dimethicone/vinyl dimethicone/methicone) crosspolymer, (dimethicone/vinyl dimethicone) crosspolymer, dimethicone crosspolymer, (diphenyl dimethicone/vinyldiphenyl dimethicone/silsesquioxane) crosspolymer, and the like.

As a silicone elastomer having an emulsifying function (also referred to as silicone surfactants), a polyether-modified silicone in which a polyoxyalkylene structure is introduced to a silicone backbone is preferably used. For example, a crosslinked silicone in which a silicone chain is crosslinked with a polyoxyalkylene chain, or a side-chain polyether-modified silicone in which a polyoxyalkylene group is introduced, as a side chain, to a silicone chain is preferable.

Specific examples of silicone elastomers having an emulsifying function include polyether-modified silicones such as PEG-10 dimethicone, PEG-9 polydimethylsiloxyethyl dimethicone, lauryl PEG-9 polydimethylsiloxyethyl dimethicone, and lauryl PEG-15 polydimethylsiloxyethyl dimethicone, and crosslinked polyether-modified silicones such as (dimethicone/(PEG-10/15)) crosspolymer and (dimethicone/polyglycerin-3) crosspolymer, among which one may be used or a mixture of two or more may be blended.

The silicone elastomer in the present invention, whether having or not having an emulsifying function, may be blended in the state of a silicone gel comprising an elastomer and a solvent. As such a silicone gel, a commercially available product may be used, including, for example, KSG-18A, KSG-16, KSG-15AP (all of the above manufactured by Shin-Etsu Chemical Co., Ltd.), Elastomer Blend DC9045 and EL7040 (manufactured by Dow Corning Toray Co., Ltd.), KSG-210, KSG-710, KSG-360Z (all of the above manufactured by Shin-Etsu Chemical Co., Ltd.), and the like.

The blended amount of the (D) silicone elastomer in the cosmetic of the present invention is normally 0.1% to 30% by mass, preferably 2% to 10% by mass, and more preferably 3% to 8% by mass. If the blended amount is less than 0.1% by mass, then the effects of blending the silicone elastomer cannot be obtained, and if more than 30% by mass is blended, then the moistness can conversely be lost.

The cosmetic of the present invention is a water-in-oil emulsion cosmetic. The oil forming the cosmetic of the present invention is not particularly limited, and may be appropriately selected from among hydrocarbon oils, ester oils, waxes, and silicone oils. In particular, silicone oils are preferable, among which it is even more preferable to blend a volatile cyclic silicone oil with a linear silicone oil from the viewpoint of the feeling in use.

The blended amount of water in the water-in-oil emulsion cosmetic of the present invention is not particularly limited, and may, for example, be approximately 30% by mass or lower, approximately 25% by mass or lower, or approximately 20% by mass.

The cosmetic of the present invention may contain other optional ingredients that can be blended into water-in-oil emulsion cosmetics within a range not inhibiting the effects of the present invention. Although the other optional ingredients are not limited, they include, for example, other powder ingredients (aside from the (A) metal soap-treated powder and the (C) spherical powder), alcohols, polyhydric alcohols, pigments, pH adjusters, humectants, thickeners (aside from the (B) water-absorbing polymer having carboxyl groups), surfactants, dispersants, stabilizers, colorants, preservatives, antioxidants, ultraviolet absorbers, fragrances, and the like.

The cosmetic of the present invention can be produced in accordance with conventional methods for producing water-in-oil emulsion cosmetics. In other words, it can be produced by stirring to emulsify water phase ingredients with separately prepared oil phase ingredients while heating as needed.

The cosmetic of the present invention is particularly suitable for use as a makeup cosmetic such as a foundation. Accordingly, the cosmetic of the present invention is preferably provided in the form of a liquid foundation, a makeup base, a BB cream, a CC cream, a cushion foundation, or the like. On the other hand, it may be provided as a skin-care cosmetic, such as a sunscreen or a milky lotion, having skin correction effects.

Examples of an impregnated body in the case of a cushion foundation include nonwoven fabrics comprising single or mixed materials such as resins, pulp, and cotton, fibrous bodies made by processing resins, foamed bodies such a sponges, porous bodies provided with continuous mechanisms, and the like. Additionally, examples of the material include NBR (acrylonitrile butadiene rubber), SBR (styrene butadiene rubber), NR (natural rubber), urethane, nylon, polyolefin, polyester, EVA (ethylene vinyl acetate), PVA (polyvinyl alcohol), silicone elastomers, and the like. However, there is no limitation to these materials as long as the impregnated body can hold contents. Among these, fibrous bodies molded by using polyester fibers, having a hardness of 40 to 60 (measured F hardness value) and a density of 0.006 to 0.1 g/cm$^3$ is preferably used.

EXAMPLES

Hereinafter, the present invention will be explained in further detail by giving examples. However, the present invention is not limited, in any way, by these examples. The blended amounts, where not especially noted, are indicated in percentage by mass relative to the total weight of the composition in which that ingredient is blended.

Water-in-oil emulsion foundations were prepared in accordance with conventional methods with the formulations indicated in Table 1 to Table 4 below. The foundation according to each example that was prepared was evaluated by a panel of experts in the categories indicated below.

Evaluation Categories:
(1) Patchiness resistance
(2) Roughness (pores etc.) correction effects
(3) Formation of aggregates of metal soap-treated powder and water-absorbing polymer Evaluation Method and Results:

Regarding (1) and (2), evaluations were made as indicated below in actual usage tests by the panel of experts.
A+: extremely superior
A: superior
B: slightly inferior
C: inferior Regarding the (3) aggregates of the metal soap-treated powder and the water-absorbing polymer, observations were made using a device (Skin Visiom (registered trademark) manufactured by Fujimic Inc.) that can evaluate the state of skin by means of images.
Aggregate formation observed="yes"
Aggregate formation not observed="no"

TABLE 1

|  | Example 1 | Example 2 | Example 3 | Example 4 | Example 5 | Example 6 |
|---|---|---|---|---|---|---|
| Decamethyl cyclopentasiloxane | 40 | 40 | 40 | 40 | 35 | 30 |
| Isopropyl myristate | 1 | 1 | 1 | 1 | 1 | 1 |
| PEG-10 dimethicone | 2.5 | 2.5 | 2.5 | 2.5 | 2.5 | 2.5 |
| Polyglyceryl-2 diisostearate | 1 | 1 | 1 | 1 | 1 | 1 |
| (PEG-15/lauryl polydimethylsiloxyethyl dimethicone) crosspolymer | 1 | 1 | 1 | 1 | 1 | 1 |
| Sodium polyacrylate starch[A] | 0.25 | 0.5 | 1 | 2 | 0.5 | 0.5 |
| Magnesium myristate-treated barium sulfate | 3 | 3 | 3 | 3 | 10 | 20 |
| Silicone-treated barium sulfate | — | — | — | — | — | — |
| Silicone-treated hydrophobic titanium oxide (fine particles) | 8 | 8 | 8 | 8 | 8 | 8 |
| Silicone-treated hydrophobic titanium oxide (pigment grade) | 3 | 3 | 3 | 3 | 3 | 3 |

TABLE 1-continued

|  | Example 1 | Example 2 | Example 3 | Example 4 | Example 5 | Example 6 |
|---|---|---|---|---|---|---|
| Silicone-treated iron oxide (red) | 0.35 | 0.35 | 0.35 | 0.35 | 0.35 | 0.35 |
| Silicone-treated iron oxide (yellow) | 1.1 | 1.1 | 1.1 | 1.1 | 1.1 | 1.1 |
| Silicone-treated iron oxide (black) | 0.05 | 0.05 | 0.05 | 0.05 | 0.05 | 0.05 |
| Nylon spherical Powder | 6 | 6 | 6 | 6 | 6 | 6 |
| Ion-exchanged water | balance | balance | balance | balance | balance | balance |
| Dynamite glycerin | 3 | 3 | 3 | 3 | 3 | 3 |
| Ethanol | 3.5 | 3.5 | 3.5 | 3.5 | 3.5 | 3.5 |
| Phenoxyethanol | 0.5 | 0.5 | 0.5 | 0.5 | 0.5 | 0.5 |
| Total | 100 | 100 | 100 | 100 | 100 | 100 |
| (1) Patchiness resistance | A | A | A | A | A | A |
| (2) Roughness correction effects | A | A | A | A | A+ | A+ |
| (3) Formation of aggregates | yes | yes | yes | yes | yes | yes |

[A]MAKIMOUSSE 25 (manufactured by Daito Kasei Kogyo Co., Ltd.)

TABLE 2

|  | Comparative Example 1 | Comparative Example 2 | Comparative Example 3 | Comparative Example 4 |
|---|---|---|---|---|
| Decamethyl cyclopentasiloxane | 40 | 40 | 40 | 30 |
| Isopropyl myristate | 1 | 1 | 1 | 1 |
| PEG-10 dimethicone | 2.5 | 2.5 | 2.5 | 2.5 |
| Polyglyceryl-2 diisostearate | 1 | 1 | 1 | 1 |
| (PEG-15/lauryl polydimethylsiloxyethyl dimethicone) crosspolymer | 1 | 1 | 1 | 1 |
| Sodium polyacrylate starch[A] | — | 0.25 | 3 | 0.5 |
| Magnesium myristate-treated barium sulfate | 3 | — | 3 | 25 |
| Silicone-treated barium sulfate | — | 3 | — | — |
| Silicone-treated hydrophobic titanium oxide (fine particles) | 8 | 8 | 8 | 8 |
| Silicone-treated hydrophobic titanium oxide (pigment grade) | 3 | 3 | 3 | 3 |
| Silicone-treated iron oxide (red) | 0.35 | 0.35 | 0.35 | 0.35 |
| Silicone-treated iron oxide (yellow) | 1.1 | 1.1 | 1.1 | 1.1 |
| Silicone-treated iron oxide (black) | 0.05 | 0.05 | 0.05 | 0.05 |
| Nylon spherical powder | 6 | 6 | 6 | 6 |
| Ion-exchanged water | balance | balance | balance | balance |
| Dynamite glycerin | 3 | 3 | 3 | 3 |
| Ethanol | 3.5 | 3.5 | 3.5 | 3.5 |
| Phenoxyethanol | 0.5 | 0.5 | 0.5 | 0.5 |
| Total | 100 | 100 | 100 | 100 |
| (1) Patchiness resistance | A+ | A+ | B | B |
| (2) Roughness correction effects | C | C | A+ | A+ |

TABLE 2-continued

|  | Comparative Example 1 | Comparative Example 2 | Comparative Example 3 | Comparative Example 4 |
|---|---|---|---|---|
| (3) Formation of aggregates | no | no | yes | yes |

(4)MAKIMOUSSE 25 (manufactured by Daito Kasei Kogyo Co., Ltd.)

As is clear from the results indicated in Table 1, Examples 1 to 4, in which the (A) metal soap-treated powder and the (B) water-absorbing polymer having carboxyl groups were blended in amounts in the ranges defined by the present invention, yielded results that were superior in all of the evaluated categories. In particular, Examples 5 and 6, in which the blended amount of magnesium myristate-treated barium sulfate was increased to 10% to 20% by mass, had extremely superior roughness correction effects. In contrast therewith, in the results indicated in Table 2, roughness correction effects were not obtained by Comparative Example 1, in which the (B) water-absorbing polymer was not blended, and Comparative Example 2, in which the (A) metal soap-treated powder was replaced with a silicone-treated powder, and as for Comparative Example 3, in which the water-absorbing polymer was blended in an amount exceeding 2% by mass, and Comparative Example 4, in which the metal soap-treated powder was blended in an amount exceeding 20% by mass, roughness correction effects were obtained, but patchiness tended to occur.

A Skin Visiom (registered trademark) was used to observe the state of skin to which the aforementioned Example 1 and Comparative Example 2 was applied. The resulting images are shown in FIG. 1. With the cosmetic of Example 1, aggregates formed by the metal soap-treated powder and the water-absorbing polymer were observed, but they were not observed in Comparative Example 2, in which it was found that texture sinking had occurred.

TABLE 3

|  | Example 7 | Example 8 | Example 9 | Comparative Example 5 | Comparative Example 6 |
|---|---|---|---|---|---|
| Decamethyl cyclopentasiloxane | 40 | 40 | 40 | 40 | 40 |
| Isopropyl myristate | 1 | 1 | 1 | 1 | 1 |
| PEG-10 dimethicone | 2.5 | 2.5 | 2.5 | 2.5 | 2.5 |
| Polyglyceryl-2 diisostearate | 1 | 1 | 1 | 1 | 1 |
| (PEG-15/lauryl polydimethylsiloxyethyl dimethicone) crosspolymer | 5 | 5 | 5 | 5 | 5 |
| Sodium polyacrylate starch(4) | 0.25 | 0.5 | 1 | — | 0.25 |
| Magnesium myristate-treated talc | 3 | 3 | 3 | 3 | — |
| Silicone-treated talc | — | — | — | — | 3 |
| Silicone-treated hydrophobic titanium oxide (fine particles) | 8 | 8 | 8 | 8 | 8 |
| Silicone-treated hydrophobic titanium oxide (pigment grade) | 3 | 3 | 3 | 3 | 3 |
| Silicone-treated iron oxide (red) | 0.35 | 0.35 | 0.35 | 0.35 | 0.35 |
| Silicone-treated iron oxide (yellow) | 1.1 | 1.1 | 1.1 | 1.1 | 1.1 |
| Silicone-treated iron oxide (black) | 0.05 | 0.05 | 0.05 | 0.05 | 0.05 |
| Nylon spherical powder | 6 | 6 | 6 | 6 | 6 |
| Ion-exchanged water | balance | balance | balance | balance | balance |
| EDTA-2Na2H$_2$O | 0.2 | 0.2 | 0.2 | 0.2 | 0.2 |
| Dynamite glycerin | 3 | 3 | 3 | 3 | 3 |
| Ethanol | 3.5 | 3.5 | 3.5 | 3.5 | 3.5 |
| Phenoxyethanol | 0.5 | 0.5 | 0.5 | 0.5 | 0.5 |
| Total | 100 | 100 | 100 | 100 | 100 |
| (1) Patchiness resistance | A | A | A | A+ | A+ |
| (2) Roughness correction effects | A+ | A+ | A+ | C | C |
| (3) Formation of aggregates | yes | yes | yes | no | no |

(4)MAKIMOUSSE 25 (manufactured by Daito Kasei Kogyo Co., Ltd.)

As indicated in Table 3, superior results were obtained in all evaluated categories even when the cores of the blended metal soap-treated powders were changed from barium sulfate to talc (Examples 7 to 9). However, roughness correction effects were not obtained in Comparative Examples 5 and 6, which did not include a water-absorbing polymer or a metal soap-treated powder.

TABLE 4

|  | Example 10 | Example 11 | Example 12 | Comparative Example 7 | Comparative Example 8 |
|---|---|---|---|---|---|
| Decamethyl cyclopentasiloxane | 40 | 40 | 40 | 40 | 40 |
| Isopropyl myristate | 1 | 1 | 1 | 1 | 1 |
| PEG-10 dimethicone | 2.5 | 2.5 | 2.5 | 2.5 | 2.5 |
| Polyglyceryl-2 diisostearate | 1 | 1 | 1 | 1 | 1 |
| (PEG-15/lauryl polydimethylsiloxyethyl dimethicone) crosspolymer | 5 | 5 | 5 | 5 | 5 |
| Crosslinked sodium carbomer(B) | 0.25 | 0.5 | 1 | — | 0.25 |
| Magnesium myristate-treated barium sulfate | 3 | 3 | 3 | 3 | — |
| Silicone-treated barium sulfate | — | — | — | — | 3 |
| Silicone-treated hydrophobic titanium oxide (fine particles) | 8 | 8 | 8 | 8 | 8 |
| Silicone-treated hydrophobic titanium oxide (pigment grade) | 3 | 3 | 3 | 3 | 3 |
| Silicone-treated iron oxide (red) | 0.35 | 0.35 | 0.35 | 0.35 | 0.35 |
| Silicone-treated iron oxide (yellow) | 1.1 | 1.1 | 1.1 | 1.1 | 1.1 |
| Silicone-treated iron oxide (black) | 0.05 | 0.05 | 0.05 | 0.05 | 0.05 |
| Nylon spherical powder | 6 | 6 | 6 | 6 | 6 |
| Ion-exchanged water | balance | balance | balance | balance | balance |
| EDTA-2Na2H$_2$O | 0.2 | 0.2 | 0.2 | 0.2 | 0.2 |
| Dynamite glycerin | 3 | 3 | 3 | 3 | 3 |
| Ethanol | 3.5 | 3.5 | 3.5 | 3.5 | 3.5 |
| Phenoxyethanol | 0.5 | 0.5 | 0.5 | 0.5 | 0.5 |
| Total | 100 | 100 | 100 | 100 | 100 |
| (1) Patchiness resistance | A+ | A+ | A+ | A+ | A+ |
| (2) Roughness correction effects | A+ | A+ | A+ | C | C |

TABLE 4-continued

|  | Example 10 | Example 11 | Example 12 | Comparative Example 7 | Comparative Example 8 |
|---|---|---|---|---|---|
| (3) Formation of aggregates | yes | yes | yes | no | no |

(B)AQUPEC MG N40R (manufactured by Sumitomo Seika Chemicals Co., Ltd.)

As is clear from the results shown in Table 4, Examples 10 to 12, in which the water-absorbing polymer was changed to crosslinked sodium carbomer (having a water absorption capacity of 10 to 500 times the weight thereof), had extremely superior patchiness resistance and roughness correction effects. In contrast therewith, roughness correction effects were not obtained for Comparative Examples 7 and 8, which did not contain a water-absorbing polymer or a metal soap-treated powder.

Other formulation examples of the water-in-oil emulsion cosmetic of the present invention will be provided. The cosmetics prepared in accordance with conventional methods using these formulations yielded evaluation results similar to those in Example 1.

Formulation Example 1: Emulsion Foundation

| Blended ingredients | | Blended amount (% by mass) |
|---|---|---|
| (1) | Volatile dimethyl polysiloxane | 30.00 |
| (2) | Decamethyl cyclopentasiloxane | 10.00 |
| (3) | Methyl polysiloxane | 3.00 |
| (4) | PEG-10 dimethicone | 1.00 |
| (5) | PEG-9 polydimethylsiloxyethyl dimethicone | 2.00 |
| (6) | Isostearic acid | 1.00 |
| (7) | bis-Butyldimethicone polyglyceryl-3 | 1.00 |
| (8) | (Dimethicone/polyglycerin-3) crosspolymer | 1.00 |
| (9) | Disteardimonium hectorite | 1.00 |
| (10) | (Vinyl dimethicone/methicone silsesquioxane) crosspolymer | 3.00 |
| (11) | (Diphenyl dimethicone/vinyl diphenyl dimethicone/silsesquioxane) crosspolymer | 2.00 |
| (12) | Hydrophobic silicone-treated fine-particle titanium oxide | 5.00 |
| (13) | Hydrophobic silicone-treated pigment-grade titanium oxide | 3.00 |
| (14) | Hydrophobic silicone-treated yellow iron oxide | 1.25 |
| (15) | Hydrophobic silicone-treated red iron oxide | 0.35 |
| (16) | Hydrophobic silicone-treated black iron oxide | 0.02 |
| (17) | Crosslinked sodium carbomer | 0.25 |
| (18) | Magnesium myristate-treated barium sulfate | 3.00 |
| (19) | Ion-exchanged water | balance |
| (20) | Dipropylene glycol | 5.00 |
| (21) | Glycerin | 3.00 |
| (22) | Preservative | 0.10 |

Formulation Example 2: Makeup Base

| Blended ingredients | | Blended amount (% by mass) |
|---|---|---|
| (1) | Volatile dimethyl polysiloxane | 25.00 |
| (2) | Decamethyl cyclopentasiloxane | 10.00 |
| (3) | Isododecane | 3.00 |
| (4) | Diphenyl siloxyphenyl trimethicone | 5.00 |
| (5) | PEG-10 dimethicone | 2.00 |
| (6) | Lauryl PEG-9 polydimethylsiloxyethyl dimethicone | 1.00 |
| (7) | (Dimethicone/polyglycerin-3) crosspolymer | 1.00 |
| (8) | Isononyl isononanoate | 3.00 |
| (9) | Disteardimonium hectorite | 1.00 |
| (10) | Spherical silica | 2.00 |
| (11) | Silylated silica | 1.00 |
| (12) | Hydrophobic silicone-treated zinc oxide | 5.00 |
| (13) | Hydrophobic silicone-treated pigment-grade titanium oxide | 2.00 |
| (14) | Hydrophobic silicone-treated yellow iron oxide | 0.12 |
| (15) | Hydrophobic silicone-treated red iron oxide | 0.17 |
| (16) | Hydrophobic silicone-treated black iron oxide | 0.01 |
| (17) | Crosslinked sodium carbomer | 0.50 |
| (18) | Magnesium myristate-treated barium sulfate | 3.00 |
| (19) | Ion-exchanged water | balance |
| (20) | 1,3-butylene glycol | 5.00 |
| (21) | Glycerin | 3.00 |
| (22) | Preservative | 0.10 |

Formulation Example 3: Sunscreen

| Blended ingredients | | Blended amount (% by mass) |
|---|---|---|
| (1) | Volatile dimethyl polysiloxane | 5.00 |
| (2) | Decamethyl cyclopentasiloxane | 25.00 |
| (3) | Octyl methoxycinnamate | 7.50 |
| (4) | PEG-10 dimethicone | 3.00 |
| (5) | Polyglyceryl-2 diisostearate | 1.00 |
| (6) | Fragrance | 0.10 |
| (7) | (Dimethicone/polyglycerin-3) crosspolymer | 1.00 |
| (8) | Cetyl ethylhexanoate | 3.00 |
| (9) | Disteardimonium hectorite | 1.00 |
| (10) | Methyl methacrylate crosspolymer | 2.00 |
| (11) | Hydrophobically treated zinc oxide | 3.00 |
| (12) | Hydrophobic silicone-treated fine-particle titanium oxide | 5.00 |
| (13) | Hydrophobic silicone-treated pigment-grade titanium oxide | 3.00 |
| (14) | Hydrophobic silicone-treated yellow iron oxide | 1.25 |
| (15) | Hydrophobic silicone-treated red iron oxide | 0.35 |
| (16) | Hydrophobic silicone-treated black iron oxide | 0.02 |
| (17) | Crosslinked sodium carbomer | 0.30 |
| (18) | Magnesium myristate-treated barium sulfate | 3.00 |
| (19) | Barium sulfate | 1.00 |
| (20) | Ion-exchanged water | balance |
| (21) | 1,3-butylene glycol | 8.00 |
| (22) | Preservative | 0.10 |

Formulation Example 4: Daytime-Use Milky Lotion

| Blended ingredients | | Blended amount (% by mass) |
|---|---|---|
| (1) | Volatile dimethyl polysiloxane | 30.00 |
| (2) | Decamethyl cyclopentasiloxane | 10.00 |

-continued

| | Blended ingredients | Blended amount (% by mass) |
|---|---|---|
| (3) | Methyl polysiloxane | 3.00 |
| (4) | PEG-10 dimethicone | 3.00 |
| (5) | Polyglyceryl-2 diisostearate | 1.00 |
| (6) | Fragrance | 0.10 |
| (7) | (Dimethicone/polyglycerin-3) crosspolymer | 1.00 |
| (8) | Isononyl isononanoate | 3.00 |
| (9) | Disteardimonium hectorite | 1.00 |
| (10) | Hydrophobic fumed silica | 1.00 |
| (11) | Crosslinked sodium carbomer | 0.30 |
| (12) | Magnesium myristate-treated barium sulfate | 3.00 |
| (13) | Ion-exchanged water | balance |
| (14) | 1,3-Butylene glycol | 8.00 |
| (15) | Glycerin | 6.00 |
| (16) | Hyaluronic acid | 0.30 |
| (17) | Preservative | 0.10 |

Production Method:

(i) The powders were added to a mixture of the oil-phase ingredients, and the result was mixed together by stirring with a homomixer or the like to obtain a powder dispersion solution (oil phase).

(ii) Next, a water phase that was premixed and placed at rest was added to the aforementioned powder dispersion solution (oil phase), and the result was mixed by stirring with a homomixer or the like to form an emulsion, thereby obtaining the product.

Finally, experimental results for a simple system, in which a metal soap-treated powder and a water-absorbing polymer having carboxyl groups were blended without including any other powder ingredients, are indicated below.

Water-in-oil emulsion preparations (Test Examples 1, 2 and 3) having the compositions indicated in Table 5 below were prepared by conventional methods. With the resulting samples, uniform films were produced by using a 0.35 mm doctor blade, and the states thereof were observed and compared.

TABLE 5

| | Test Example 1 | Test Example 2 | Test Example 3 |
|---|---|---|---|
| Decamethyl cyclopentasiloxane | 40 | 40 | 40 |
| Isopropyl myristate | 1 | 1 | 1 |
| PEG-10 dimethicone | 2.5 | 2.5 | 2.5 |
| Polyglyceryl-2 diisostearate | 1 | 1 | 1 |
| (PEG-15/lauryl polydimethylsiloxyethyl dimethicone) crosspolymer | 1 | 1 | 1 |
| Sodium polyacrylate starch[4] | 0.25 | — | 0.25 |
| Magnesium myristate-treated barium sulfate | 3 | 3 | — |
| Ion-exchanged water | balance | balance | balance |
| Dynamite glycerin | 3 | 3 | 3 |

TABLE 5-continued

| | Test Example 1 | Test Example 2 | Test Example 3 |
|---|---|---|---|
| Ethanol | 3.5 | 3.5 | 3.5 |
| Phenoxyethanol | 0.5 | 0.5 | 0.5 |
| Total | 100 | 100 | 100 |
| (3) Formation of aggregates | yes | no | no |

[4]MAKIMOUSSE 25 (manufactured by Daito Kasei Kogyo Co., Ltd.)

Figure 2:
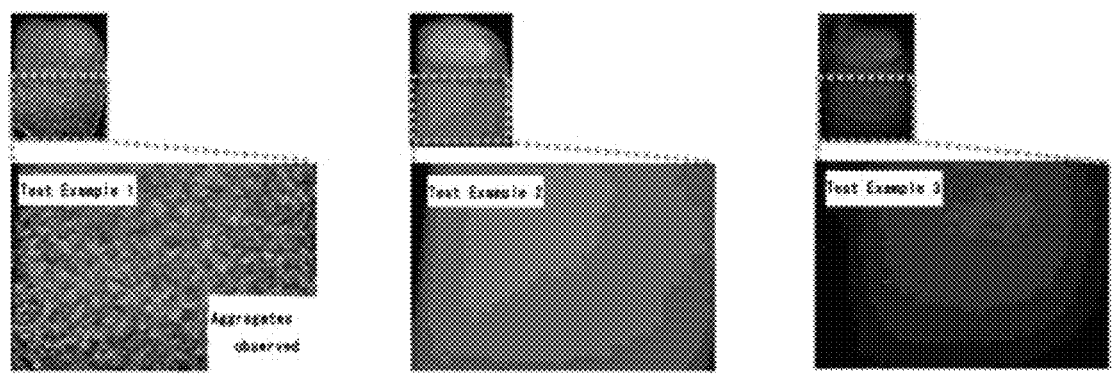
FIG. 2 is a drawing showing the outer appearances of thin films formed from the formulations of Test Examples 1 to 3.

As indicated in FIG. 2, aggregates were not observed in Test Examples 2 and 3, in which only one of the metal soap-treated powder and the water-absorbing polymer having carboxyl groups was blended, whereas aggregates that were visible to the naked eye were observed in Test Example 1, in which both the metal soap-treated powder and the water-absorbing polymer having carboxyl groups were blended.

Figure 3:
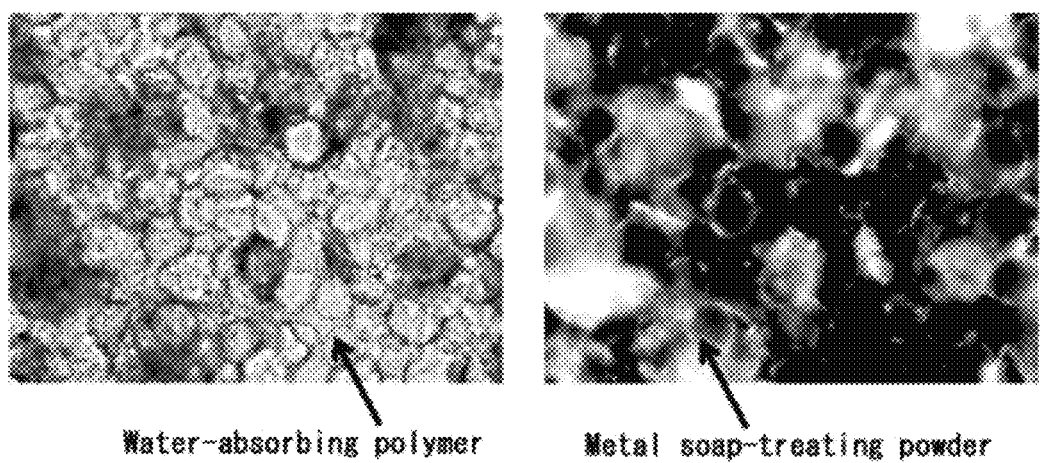
FIG. 3 is a drawing showing a microscope photograph of the thin film of Test Example 1 (left side: normal mode, right side: polarized mode).

FIG. 3 is an image of a detailed observation of Test Example 1 using an optical microscope. It can be seen that aggregates (structures) in which water-absorbing polymers having carboxyl groups that have absorbed water are extremely close to metal soap-treated powders are formed.

The invention claimed is:

1. A water-in-oil emulsion cosmetic comprising:
   (A) 0.5% to 15% by mass of an extender pigment treated with a metal soap;
   (B) 0.01% to 2% by mass of a water-absorbing polymer having carboxyl groups, and
   (C) 30% by mass or less of water, wherein the cosmetic comprises aggregates formed between (a) the water-absorbing polymer that absorbed water and (b) the extender pigment treated with the metal soap.

2. The cosmetic as in claim 1, wherein the (B) water-absorbing polymer having carboxyl groups has a water absorption capacity of 10 times to 1000 times the weight thereof.

3. The cosmetic as in claim 1, wherein the metal soap is selected from the group consisting of magnesium myristate, zinc myristate, and aluminum myristate.

4. The cosmetic as in claim 1, wherein the extender pigment is mica, talc or barium sulfate.

5. The cosmetic as in claim 1, wherein the (B) water-absorbing polymer having carboxyl groups is sodium poly(acrylic acid) or sodium polyacrylate starch.

6. The cosmetic as in claim 2, wherein the (B) water-absorbing polymer having carboxyl groups has a water absorption capacity of 10 times to 500 times the weight thereof.

7. The cosmetic of claim 1, wherein the metal soap is selected from the group consisting of magnesium myristate, zinc stearate and aluminum stearate and the water-absorbing polymer having carboxyl groups is sodium poly(acrylic acid) or sodium polyacrylate starch.

8. The cosmetic of claim 7, wherein the extender pigment is mica, talc or barium sulfate.

9. The cosmetic of claim 1, wherein the metal soap is magnesium myristate and the water-absorbing polymer having carboxyl groups is sodium poly(acrylic acid) or sodium polyacrylate starch.

10. The cosmetic of claim 9, wherein the extender pigment is mica, talc or barium sulfate.

* * * * *